United States Patent
Ertl et al.

(10) Patent No.: US 6,686,177 B1
(45) Date of Patent: Feb. 3, 2004

(54) INSULIN ANALOGS WITH ENHANCED ZINC BINDING

(75) Inventors: Johann Ertl, Bremthal (DE); Paul Habermann, Eppstein (DE); Karl Geisen, Frankfurt (DE); Gerhard Seipke, Hogheim (DE); Axel Wollmer, Aachen (DE)

(73) Assignee: Aventis Pharma Deutschland GmbH (DE)

( * ) Notice: Subject to any disclaimer, the term of this patent is extended or adjusted under 35 U.S.C. 154(b) by 0 days.

(21) Appl. No.: 09/701,968

(22) PCT Filed: May 21, 1999

(86) PCT No.: PCT/EP99/03490

§ 371 (c)(1),
(2), (4) Date: May 14, 2001

(87) PCT Pub. No.: WO99/64598

PCT Pub. Date: Dec. 16, 1999

(30) Foreign Application Priority Data

Jun. 6, 1998 (DE) .......................................... 198 25 447

(51) Int. Cl.⁷ ........................ A61K 38/28; C07K 14/62; C12N 15/17; C12N 15/64; C12N 1/21

(52) U.S. Cl. .................. 435/69.4; 435/243; 435/320.1; 435/325; 514/3; 514/866; 530/303

(58) Field of Search .............................. 530/303; 514/3, 514/866; 435/69.4, 320.1, 325, 243

(56) References Cited

U.S. PATENT DOCUMENTS

| | | | |
|---|---|---|---|
| 4,476,118 A | | 10/1984 | Brange et al. |
| 4,569,794 A | * | 2/1986 | Smith et al. |
| 4,701,440 A | | 10/1987 | Grau |
| 5,008,241 A | | 4/1991 | Markussen et al. |
| 5,177,058 A | | 1/1993 | Dörschug |
| 5,227,293 A | | 7/1993 | Stengelin et al. |
| 5,284,933 A | | 2/1994 | Döbeli et al. |
| 5,310,663 A | | 5/1994 | Döbeli et al. |
| 5,358,857 A | | 10/1994 | Stengelin et al. |
| 5,656,722 A | | 8/1997 | Dörschug |
| 6,221,837 B1 | * | 4/2001 | Ertl et al. |

FOREIGN PATENT DOCUMENTS

| | | |
|---|---|---|
| DE | 37 39 347 A1 | 6/1989 |
| EP | 0 600 372 A1 | 6/1984 |
| EP | 0 180 920 A2 | 5/1986 |
| EP | 0 184 355 B1 | 6/1986 |
| EP | 0 211 299 A2 | 2/1987 |
| EP | 0 227 938 A2 | 7/1987 |
| EP | 0 229 998 A2 | 7/1987 |
| EP | 0 286 956 A2 | 10/1988 |
| EP | 0 305 760 A2 | 3/1989 |
| EP | 0 347 781 A2 | 12/1989 |
| EP | 0 368 187 A2 | 5/1990 |
| EP | 0 453 969 A1 | 10/1991 |
| EP | 0 668 292 A2 | 8/1995 |
| WO | WO 91/03550 | 3/1991 |

OTHER PUBLICATIONS

D.T. Manallack et al., "Design, Synthesis, and Testing of Insulin Hexamer–Stabilizing Agents," *J. Med. Chem.* 28:1522–1526 (1985).

C. Ljungquist et al., "Immobilization and Affinity Purfication of Recombinant Proteins Using Histidine Peptide Fusions," *Eur. J. Biochem.* 186:563–569 (1989).

J.H. Karam, "Pancreatic Hormones & Antidiabetic Drugs," in *Basic & &i Clinical Pharmacology 5th Edition*, B.G. Katzung, Ed., Appleton & Lange, Norwalk, Conn., pp. 586–587 (1992).

J. Brang et al., "Monomeric Insulins and Their Experimental and Clinical Implications," *Diabetes Care* 13(9): 923–54 (1990).

S. Kang et al., "Subcutaneous Insulin Absorption Explained by Insulin's Physicochemical Properties: Evidence From Absorption Studies of Soluble Human Insulin and Insulin Analogues in Humans," *Diabetes Care* 14: 943–8 (1991).

G.D. Smith et al., "Structural Stability in the 4–Zinc Human Insulin Hexamer," *Proc. Nat'l. Acad. Sci. USA* (81) 7093–7 (1984).

R.C. Marshall et al., "Protein Oligomer Composition, Preparation of Monomers and Constituent Chains," in *Practical Protein Chemistry–A Handbook*, A. Darbre, Ed., pp. 49–53 (1986).

G.H. Dixon et al., "Regeneration of Insulin Activity from the Separated and Inactive A and B Chains," *Nature* 188: 721–4 (1960).

W. Kemmler et al., "Studies on the Conversion of Proinsulin to Insuli. I. Conversion *In Vitro* with Trypsin and Carboxypeptidase B," *J. Biol. Chem.* 246(22): 6786–91 (1971).

M.C. Smith et al., "Chelating Peptide–immobilized Metal Ion Affinity Chromatography," *J. Biol. Chem.* 263(15): 7211–5 (1988).

* cited by examiner

Primary Examiner—Christine J. Saoud
(74) Attorney, Agent, or Firm—Finnegan, Henderson, Farabow, Garrett & Dunner, L.L.P.

(57) ABSTRACT

The invention relates to insulin analogs exhibiting enhanced zinc binding capacity and to stable zinc complexes thereof having a retarded activity in comparison with human insulin. The invention further relates to a method for the production of said insulin analogs and to their use, particularly in pharmaceutical preparations for therapy of type I and type II diabetes mellitus.

44 Claims, No Drawings

INSULIN ANALOGS WITH ENHANCED ZINC BINDING

This application is the National Stage of International Application No. PCT/EP99/03490, filed May 21, 1999, which claims priority to German Application No. 198 25 447.4, filed Jun. 6, 1998.

The present invention relates to insulin analogs which have an increased zinc binding ability, and to stable zinc complexes thereof which, in comparison with human insulin, have a delayed profile of action, to a process for their preparation and to their use, in particular in pharmaceutical preparations for the therapy of diabetes mellitus of type I and also type II.

Worldwide, approximately 120 million people suffer from diabetes mellitus. Among these, approximately 12 million are type I diabetics, for whom the substitution of the lacking endocrine insulin secretion is the only possible therapy at present. Those affected are prescribed insulin injections, as a rule several times daily, for life. Unlike type I diabetes, in type II diabetes there is not fundamentally a lack of insulin, but in a large number of cases, especially in the advanced stage, treatment with insulin, if appropriate in combination with an oral antidiabetic, is regarded as the most favorable form of therapy.

In healthy people, the release of insulin by the pancreas is strictly coupled to the concentration of the blood glucose. Increased blood glucose levels, such as occur after meals, are rapidly compensated by a corresponding increase in insulin secretion. In the fasting state, the plasma insulin level drops to a basal value which is sufficient to guarantee a continuous supply of insulin-sensitive organs and tissues with glucose and to keep the hepatic glucose production low during the night. The replacement of the endogenous insulin secretion by exogenous, mostly subcutaneous, administration of insulin as a rule does not nearly achieve the quality of the physiological regulation of the blood glucose described above. Frequently, there are losses of control of the blood glucose upward or downward, which in their most severe forms can be life-threatening. In addition, blood glucose levels which have been raised for years without initial symptoms, however, also represent a considerable risk to health. The large-scale DCCT study in the USA (The Diabetes Control and Complications Trial Research Group (1993) N, Engl. J. Med. 329, 977–986) clearly demonstrated that chronically raised blood glucose levels are largely responsible for the development of diabetic late damage. Diabetic late damage is micro- and macrovascular damage which is manifested, under certain circumstances, as retinopathy, nephropathy, or neuropathy and leads to blindness, kidney failure and the loss of extremities and is moreover accompanied by a high risk of cardiovascular diseases. It can be derived from this that an improved therapy of diabetes must primarily aim to keep the blood glucose as closely as possible in the physiological range. According to the concept of intensified insulin therapy, this should be achieved by a number of daily injections of rapid- and slow-acting insulin preparations. Rapid-acting formulations are given at mealtimes in order to level out the post-prandial increase in blood glucose. Slow-acting basal insulins should ensure the basic supply of insulin, in particular during the night, without leading to hypoglycemia.

The basal insulins available at present fulfill this requirement only inadequately. The frequently used NPH insulins especially have a too strongly pronounced maximum action and have too short an overall action. In the case of administration in the evening, this involves the risk of nightly hypoglycemia and morning hyperglycemia.

EP 0 821 006 discloses insulin analogs having increased zinc binding ability, which in combination with zinc have a delayed profile of action compared with human insulin. These analogs differ from human insulin essentially by variation of the amino acid in position A21 of the A chain and by addition of a histidine residue or of a peptide having 2 to 35 amino acid residues, which contains 1 to 5 histidine residues, in position B30 of the B chain.

It is the object of the present invention to provide further insulin analogs (analogs of human or animal insulin) which have an increased zinc binding ability, form a stable complex comprising a hexamer of the insulin analog and zinc, and, in a suitable preparation, make possible an improved therapy of diabetes mellitus of type I and of type II on subcutaneous injection as a result of the profile of action, which is delayed in comparison with human insulin.

Insulin analogs are derived from naturally occurring insulins, namely human insulin (see SEQ ID NO: 1: A chain of human insulin and SEQ ID NO: 2: B chain of human insulin) or animal insulins by substitution or absence of at least one naturally occurring amino acid residue and/or addition of at least one amino acid residue to the A and/or B chain of the naturally occurring insulin.

1. An insulin analog or a physiologically tolerable salt thereof of the formula I

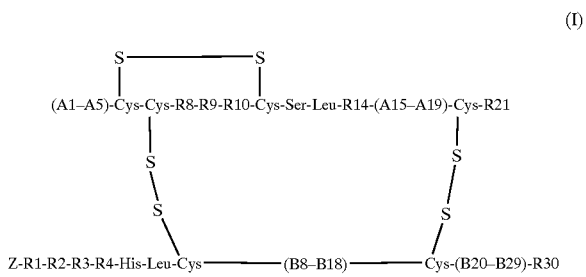

in which (A1–A5) are the amino acid residues in the positions A1 to A5 of the A chain of human insulin (cf. SEQ ID NO: 1) or animal insulin, (A15–A19) are the amino acid residues in the positions A15 to A19 of the A chain of human insulin (cf. SEQ ID NO: 1) or animal insulin, (B8–B18) are the amino acid residues in the positions B8 to B18 of the B chain of human insulin (cf. SEQ ID NO: 2) or animal insulin, (B20–B29) are the amino acid residues in the positions B20 to B29 of the B chain of human insulin (cf. SEQ ID NO: 2) or animal insulin, R8 is Thr or Ala, R9 is Ser or Gly, R10 is Ile or Val, R14 is Tyr, His, Asp or Glu, R21 is Asn, Asp, Gly, Ser, Thr, Ala, Glu or Gln, R1 is any desired genetically encodable amino acid residue, absent or a hydrogen atom, R2 is Val, Ala or Gly, R3 is Asn, His, Glu or Asp, R4 is Ala, Ser, Thr, Asn, Asp, Gln, Gly or Glu, R30 is any desired genetically encodable amino acid residue or —OH, Z is a hydrogen atom or a peptide residue having 1 to 4 genetically encodable amino acid residues, comprising 1 to 4 histidine residues (His), with the proviso that at least one of the following is true: (1) when Z is a hydrogen atom, R1 or R3 is chosen from His, Glu, and Asp; (2) when R1 is a neutral or negatively charged amino acid residue, R3 is His; or (3) when Z is a hydrogen atom, R14 is chosen from His, Asp and Glu; and with the further proviso that when in formula I R3, R3 in combination with R21, or R3 in combination with R4 differs from human insulin, the insulin analog or the physiologically tolerable salt thereof of the formula I contains at least one additional variation from human insulin. (cf. SEQ ID NO: 1 and SEQ ID NO: 2).

Preferably, the insulin analog or the physiologically tolerable salt thereof is one wherein 2. R8 is Thr, R9 is Ser and R10 is Ile,
3. R1 is Phe, His, Asn, Asp or Gly,
4. R30 is Thr, Ala or Ser or
5. wherein R21 is Asn and R1 is Phe.
6. A preferred embodiment of the present invention is an insulin analog or a physiologically tolerable salt thereof of the formula 1, wherein R2 is Val, R3 is Asn and R4 is Gln.

An insulin analog or a physiologically tolerable salt thereof of the formula I is furthermore preferred which is distinguished in that R14 is 7. Tyr,
8. His,
9. Asp or
10. Glu.

An insulin analog or a physiologically tolerable salt thereof of the formula I is furthermore preferred which is distinguished in that R30 is 11. Thr,
12. Ala,
13. Ser or
14. —OH.

An insulin analog or a physiologically tolerable salt thereof of the formula I is furthermore preferred which is distinguished in that Z is 15. His,
16. His-Ala- or
17. His-Ala-Ala-.

Examples of insulin analogs according to the present invention are 18. an insulin analog or a physiologically tolerable salt thereof of the formula I, which is distinguished in that the B chain has the sequence
   His Phe Val Asn Gln His Leu Cys Gly Ser His Leu Val Glu Ala Leu Tyr Leu Val Cys Gly Glu Arg Gly Phe Phe Tyr Thr Pro Lys
   (SEQ ID NO: 3), for example His(B0), des(B30) human insulin,
19. an insulin analog or a physiologically tolerable salt thereof of the formula I, which is distinguished in that the B chain has the sequence
   His Phe Val Asn Gln His Leu Cys Gly Ser His Leu Val Glu Ala Leu Tyr Leu Val Cys Gly Glu Arg Gly Phe Phe Tyr Thr Pro Lys Thr
   (SEQ ID NO: 4), for example His(B0)-human insulin,
20. an insulin analog or a physiologically tolerable salt thereof of the formula I, which is distinguished in that the B chain has the sequence
   His Ala Phe Val Asn Gln His Leu Cys Gly Ser His Leu Val Glu Ala Leu Tyr Leu Val Cys Gly Glu Arg Gly Phe Phe Tyr Thr Pro Lys Thr
   (SEQ ID NO: 5), for example His(B-1), Ala(B0) human insulin or
21. an insulin analog or a physiologically tolerable salt thereof of the formula I, which is distinguished in that the B chain has the sequence
   His Ala Ala Phe Val Asn Gln His Leu Cys Gly Ser His Leu Val Glu Ala Leu Tyr Leu Val Cys Gly Glu Arg Gly Phe Phe Tyr Thr Pro Lys Thr
   (SEQ ID NO: 6), for example His(B-2), Ala(B-1), Ala(B0)-human insulin.

The present invention furthermore relates to a process for the preparation of the insulin analog or of a physiologically tolerable salt thereof according to the present invention, comprising the construction of a replicable expression vehicle which contains a DNA sequence which codes for a precursor of the insulin analog having the amino acid sequence of formula II $$\text{Met-}X^2_m\text{-(Arg)}_p\text{-Z-R1-R2-R3-R4-His-Leu-Cys-(B8–B18)-Cys-(B20–B29)-R30-}X^1_n\text{-Arg-(A1–A5)-Cys-Cys-R8-R9-R10-Cys-Ser-Leu-R14-(A15–A19)-Cys-R21} \quad \text{II}$$

in which
   $X^1_n$ is a peptide chain having n amino acid residues, where n is an integer from 0 to 34,
   $X^2_m$ is a peptide chain having m amino acid residues, where m is an integer from 0 to 20,
   p is 0, 1 or 2,
   R30 is any desired genetically encodable amino acid residue or is absent and
   Z is absent or is a peptide residue having 1 to 4 genetically encodable amino acid residues, comprising 1 to 4 histidine residues (His)
and the other variables have the meanings mentioned above under No. 1, where the abovementioned provisos also apply, expression in a host cell and release of the insulin analog from its precursor using chemical and/or enzymatic methods.

The host cell is preferably a bacterium, particularly preferably the bacterium *E. coli*.

The host cell is preferably a yeast, particularly preferably *Saccharomyces cerevisiae*.

During expression in *E. coli*, the fusion proteins mentioned (SEQ ID NO: 7 to 9) as a rule form insoluble inclusion bodies, which can be isolated by centrifugation after cell disruption and are dissolved again using chaotropic additives (e.g. 8 M urea or 6 M guanidinium chloride). The dissolved fusion protein can be subjected to sulfitolysis, in which SH radicals are converted into S-sulfonates (e.g. R. C. Marshall and A. S. Iglis in, Practical Protein Chemistry—A Handbook', edited by A. Darbre (1986), pages 49–53). The solubility of the fusion protein is thereby improved and purification, for example by means of anion-exchange or gel permeation chromatography, is facilitated.

The conversion of the derivatized fusion protein into preproinsulin with a native spatial structure and correctly formed disulfide bridges (folding) is carried out in dilute aqueous solution by addition of a limited amount of an SH reagent such as mercaptoethanol, cysteine or glutathione and subsequent aerial oxidation. Alternatively, the dissolved, underivatized fusion protein can also be directly folded under similar conditions (EP-A-0 600 372; EP-A-0 668 292).

Preproinsulin is then converted into biologically active insulin by limited proteolytic cleavage. For this, it is possible to use trypsin which removes the presequence indicated in formula II by Met-$X^2_m$-$(Arg)_p$ and cleaves at the peptide chain indicated by $X^1_n$-Arg and thus separates the B and A chain. As a rule, the sequence $X^1$ begins with Arg, $Arg_2$ or it is not present (n=0), so that after the cleavage an insulin derivative is present which is prolonged by Arg or $Arg_2$ at the C terminus of the B chain. These amino acids can be removed using carboxypeptidase B. The tryptic cleavage can also be carried out by increasing the trypsin concentration or prolonging the reaction time such that cleavage additionally takes place at lysine(B29). In this case, a des(B30) insulin derivative results.

The insulin analog formed during the cleavage can be purified by standard chromatographic procedures (e.g. ion-exchange and reversed phase chromatography) and finally isolated by precipitation, crystallization or simple freeze-drying.

The precursor of the insulin analog preferably has the sequence

Met Ala Thr Thr Ser Thr Gly Asn Ser Ala Arg His Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn (SEQ ID NO: 7), for example the sequence of His(B0)-preproinsulin, or the sequence Met Ala Thr Thr Ser Thr Gly Asn Ser Ala Arg His Ala Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn (SEQ ID NO: 8), for example the sequence of His(B-1), Ala(B0) preproinsulin, or the sequence Met Ala Thr Thr Ser Thr Gly Asn Ser Ala Arg His Ala Ala Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Pro Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn (SEQ ID NO: 9), for example the sequence of His(B-2), Ala(B-1), Ala(B0)-preproinsulin.

The present invention also relates to the abovementioned precursors of the insulin analogs according to the present invention, in particular the preproinsulins, the DNA sequences which code for a precursor of the insulin analog according to the present invention, the expression vehicles which contain a DNA sequence which codes for a novel precursor of the insulin analog according to the present invention, and a host cell which is transformed using such an expression vehicle.

The present invention furthermore relates to a pharmaceutical preparation comprising at least one insulin analog and/or at least one physiologically tolerable salt according to the present invention.

Preferably, the pharmaceutical preparation is distinguished in that it contains the insulin analog according to the invention and/or the physiologically tolerable salt thereof in dissolved, amorphous and/or crystalline form.

The pharmaceutical preparation alternatively furthermore contains a depot auxiliary, preferably protamine sulfate, the insulin analog and/or the physiologically tolerable salt thereof preferably being present in a cocrystallizate with the protamine sulfate.

The pharmaceutical preparation according to the present invention can alternatively additionally contain unmodified human insulin and/or a further insulin analog, preferably Gly(A21)-Arg(B31)-Arg(B32)-human insulin.

The present invention furthermore relates to an injectable solution having insulin activity, which contains the pharmaceutical preparation according to the present invention in dissolved form, preferably containing 1 µg to 2 mg of zinc per ml, particularly preferably containing 5 µg to 200 µg of zinc per ml.

The present invention furthermore relates to the use of the insulin analog and/or its physiologically tolerable salt according to the present invention for the production of a pharmaceutical preparation which has an insulin activity having a delayed onset of action.

The object set at the outset is furthermore achieved by an insulin-zinc complex, comprising an insulin hexamer and 4 to 10 zinc ions per insulin hexamer, wherein the insulin hexamer consists of six molecules of an insulin analog of the formula I

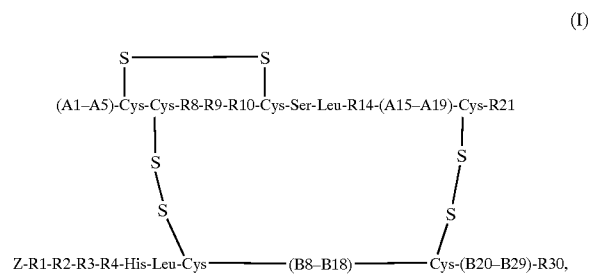

in which
(A1–A5) are the amino acid residues in the positions A1 to A5 of the A chain of human insulin or animal insulin,
(A15–A19) are the amino acid residues in the positions A15 to A19 of the A chain of human insulin or animal insulin,
(B8–B18) are the amino acid residues in the positions B8 to B18 of the B chain of human insulin or animal insulin,
(B20–B29) are the amino acid residues in the positions B20 to B29 of the B chain of human insulin or animal insulin,
R8 is Thr or Ala,
R9 is Ser or Gly,
R10 is Ile or Val,
R14 is Tyr, His, Asp or Glu,
R21 is Asn, Asp, Gly, Ser, Thr, Ala, Glu or Gln,
R1 is any desired genetically encodable amino acid residue, absent or a hydrogen atom, R2 is Val, Ala or Gly, R3 is Asn, His, Glu or Asp, R4 is Ala, Ser, Thr, Asn, Asp, Gln, Gly or Glu, R30 is any desired genetically encodable amino acid residue or —OH, Z is a hydrogen atom or a peptide residue having 1 to 4 genetically encodable amino acid residues, comprising 1 to 4 histidine residues (His).

The insulin-zinc complex preferably contains 5 to 8 zinc ions per insulin hexamer.

The insulin-zinc complex preferably contains an insulin hexamer which consists of six molecules of the insulin analog of the formula I described above according to the present invention.

The insulin-zinc complex according to the present invention is preferably also one wherein the B chain of the insulin analog of the formula I has the sequence Phe Val His Gln His Leu Cys Gly Ser His Leu Val Glu Ala Leu Tyr Leu Val Cys Gly Glu Arg Gly Phe Phe Tyr Thr Pro Lys Thr (SEQ ID NO: 10), for example His(B3)-human insulin, or wherein the B chain of the insulin analog of the formula I has the sequence Phe Val Asp Gln His Leu Cys Gly Ser His Leu Val Glu Ala Leu Tyr Leu Val Cys Gly Glu Arg Gly Phe Phe Tyr Thr Pro Lys Thr (SEQ ID NO: 11), for example Asp(B3)-human insulin.

The present invention also relates to a pharmaceutical preparation, comprising at least one insulin-zinc complex according to the invention and a pharmaceutical preparation comprising an acidic solution of at least one insulin analog and/or a physiologically tolerable salt thereof with an appropriate amount of zinc ions, which makes possible the formation of an insulin-zinc complex according to the present invention, the insulin analog and/or the physiologically tolerable salt preferably containing the insulin analog of the formula I according to the present invention described above or an insulin analog of the formula I whose B chain has the sequence with the number SEQ ID NO's.: 3, 4, 5, 10 or 11.

The pharmaceutical preparation is preferably one which comprises the insulin-zinc complex in dissolved, amorphous and/or crystalline form.

The present invention also relates to an injectable solution having insulin activity, comprising the pharmaceutical preparation in dissolved form and preferably contains 1 $\mu$g to 2 mg of zinc per ml, particularly preferably contains 5 $\mu$g to 200$\mu$g of zinc per ml.

The present invention also relates to the use of the insulin-zinc complex for the production of a pharmaceutical preparation which has an insulin activity having a delayed onset of action.

The insulin analogs according to the present invention are biologically active and exhibit a strongly delayed action after subcutaneous administration as a weakly acidic, clear solution containing 80 $\mu$g of $Zn^{++}$/ml (zinc/ml) in the dog. In the case of the insulin analog which is prolonged at the N-terminus of the B chain by histidine, His(B0), des(B30) human insulin (see SEQ ID NO.: 3), the profile of action depends, for example, very strongly on the amount of added zinc ions. A zinc-free preparation has no depot effect at all (total action 6–8 h, Example 8) and hardly differs in its pharmacodynamics from human insulin, while after addition of zinc ions (80 $\mu$g/ml), a strong delay in action is found (total action approximately 16 h, Example 8). The observed depot effect is thus significantly more marked than that of NPH-insulin. Moreover, this analog has the advantage that the pharmacodynamics can be controlled by prespecification of the zinc content within a range which is not possible with human insulin. Formulations having a rapid onset of action can be prepared just like those having a moderately or strongly delayed action with an active substance just by varying the zinc content. Thus the profile of action can be individually adapted to the needs of the patient, either using a preparation having an appropriately preset zinc content or by mixing of preparations having a high and low zinc content by the physician or the patients themselves.

The analogs described here are furthermore those which, in comparison to human insulin, have an increased affinity for zinc ions.

In aqueous neutral solution, human insulin forms hexamers which in each case complex two zinc ions via the His(B10) side chains. These zinc ions cannot be removed by dialysis against aqueous buffers in neutral solution. Under the same conditions, the analogs described here bind more than 4 zinc ions. In the case of the His(B0)-des(B30)- and His(B3)-insulin according to the invention, these are approximately 7 zinc ions/hexamer; in the case of Asp(B3) insulin 4.2 zinc ions/hexamer were measured (Example 9).

It is known that in neutral solutions zinc leads to the formation of relatively high molecular weight associates and to the precipitation of the insulin. After the injection of a weakly acidic zinc-containing preparation which contains insulin which is dissolved to give a clear solution, the formation of insulin-zinc complexes and, as a result, the precipitation of the insulin occur in the subcutaneous tissue due to neutralization. Insulin goes into solution again from this depot and then passes into the blood stream and to the site of action with a delay. This delay in action is only slight in the case of human insulin, but strongly developed in the case of the analogs described here on account of the increased affinity for zinc. The increased zinc binding is therefore the basis of the zinc-dependent prolongation of action described above.

The present invention therefore not only relates to the insulin analogs described but also to the associated insulin-zinc complexes. These complexes differ from the corresponding human insulin-zinc complexes in that they have a higher content of firmly bound zinc. It is therefore evident that in addition to zinc other transition metal ions such as, for example, cobalt or copper can also be employed for the formation of corresponding complexes.

EXAMPLE 1

Construction of the Plasmid pINT345d Coding for the Variant His(B3)-preproinsulin The US patent having the U.S. Pat. No. 5,358,857 incorporated herein by reference describes the plasmid pINT90d. DNA of this plasmid is used as a starting material for the construction of the plasmid pINT345d, which is characterized by two new properties compared with pINT90d. On the one hand, it codes for a preproinsulin analog which contains the amino acid histidine instead of asparagine in position 3 of the B chain and on the other hand it carries a recognition sequence for the restriction enzyme BssH2 immediately before the start of the sequence coding for this preproinsulin variant, so that the sequence coding for the N-terminal 10 amino acids of the preproinsulin analog can be easily manipulated if the Dra3 cleavage site in the course of the preproinsulin sequence is taken into account. For the construction of the plasmid pINT345d, DNA of the plasmid pINT90d is cleaved in position 284 bp by the restriction enzyme Ncol and in position 351 bp by the restriction enzyme Dra3 in a double digestion mixture so that two fragments are formed. After separation of the cleavage mixture by gel electrophoresis, the large residual plasmid DNA fragment is isolated.

This DNA fragment is then reacted with the synthetic DNA fragment of the form

```
                                                                                    (SEQ ID NO 12)
       ½ Ncol                                BssH2  B1  B2  His B4  B5  B6  B7  B8  B9  ½ Dra3
5'- C ATG GCA ACA ACA TCA ACA GGA AAT TCG GCG CGC TTT GTG CAC CAG CAC CTG TGG GGC TCC CAC CTA - 3'

3'-       CGT TGT TGT AGT TGT CCT TTA AGC CGC GCG AAA CAC GTG GTC GTG GAC ACG CCG AGG GTG     -5'
``` in a T4-DNA ligase reaction. Competent *E.coli* K12 cells are transformed with the ligation mixture and the transformation mixture is plated out onto NA plates which contain 20mg/l ampicillin. The plates are incubated at 37° C. overnight. Plasmid DNA is isolated from resulting colonies and cleaved using the restriction enzyme BssH2. The desired plasmid DNA is linearized in the course of this and thus differs from pINT90d DNA which contains no BssH2 cleavage site and accordingly is not cleaved.

The plasmid DNA of a clone which behaves correctly is designated by pINT345d.

It is used as a starting material for the construction of the preproinsulin variants described below.

EXAMPLE 2

Construction of the Plasmid pINT342d Coding for the Variant His(B0)-preproinsulin DNA of the plasmid pINT345d is double-digested with the enzymes BssH2 and Dra3 and the large residual plasmid fragment is isolated after separation by gel electrophoresis. This DNA fragment is reacted with the synthetic DNA fragment of the form

```
                                                         (SEQ ID NO 13)
           His B1  B2  B3  B4  B5  B6  B7  B8  B9  B10
5'- CG CGC CAC TTT GTT AAC CAG CAC CTG TGC GGC TCC CAC CTA -3'

3'-      G GTG AAA CAA TTG GTC GTG GAC ACG CCG AGG GTG    -5'
   ½ BssH2        Hpa1                              ½ Dra3
``` in a T4 DNA ligase reaction. The plasmid pINT342d is formed, which comprises an additional Hpa1 cleavage site compared with the starting plasmid. The plasmid codes for a preproinsulin variant which has a histidine in position B0.

EXAMPLE 3

Construction of the Plasmid pINT343d Coding for the Variant His(B-1), Ala(B0)-preproinsulin DNA of the residual plasmid fragment described in Example 2 is reacted with a synthetic DNA fragment of the form

```
                                                              (SEQ ID NO 14)
           His Ala B1  B2  B3  B4  B5  B6  B7  B8  B9  B10 B11
5'- CG CGC CAC GCT TTT GTT AAC CAG CAC CTG TGC GGC TCC CAC CTA -3'

3'-      G GTG CGA AAA CAA TTG GTC GTG GAC ACG CCG AGG GTG    -5'
   ½ BssH2            Hpa1                                  ½ Dra3
``` in a T4 DNA ligase reaction. The plasmid pINT343d is formed, which, like pINT342d, also contains an additional Hpa1 cleavage site compared with the starting vector.

EXAMPLE 4

Construction of the Plasmid pINT344d Coding for the Variant His(B-2),Ala(B-1),Ala(B0)-preproinsulin DNA of the residual plasmid fragment described in Example 2 is reacted with a synthetic DNA fragment of the form

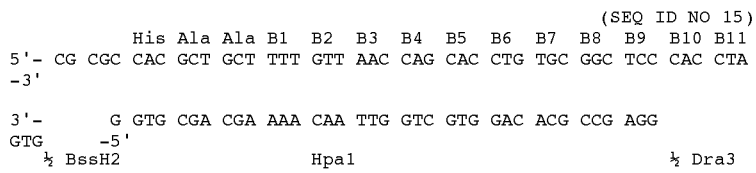

in a T4 DNA ligase reaction. The plasmid pINT344d results, which comprises an additional Hpa1 cleavage site compared with the starting vector.

EXAMPLE 5

Expression of the Constructed Insulin Variants

The plasmids pINT 342d, 343d and 344d are, by way of example, in each case transformed into *E.coli* K12 W3110. Recombinant bacteria which contain the plasmids for the respective variant are then fermented according to Example 4 of the US patent having the U.S. Pat. No. 5,227,293 incorporated herein by reference and the desired raw material for the production of the respective insulin variant is thus produced.

EXAMPLE 6

Preparation of His(B0),des(B30)-insulin

According to Example 5, the preproinsulin variant is expressed in *E.coli* and isolated in the form of inclusion bodies after cell disruption by centrifugation. The inclusion bodies are dissolved in urea (8 mol/l), subjected to sulfitolysis and purified by anion exchange (Q-Sepharose) and gel permeation chromatography (Sephacryl S 200). The buffers employed in the chromatography contain 4 M urea and 50 mM Tris/HCl (tris(hydroxymethyl)aminomethane/HCl) pH 8.5. The fractional elution on the anion exchanger is carried out by applying a gradient of 0 to 0.5 M NaCl. The concentration of the urea is then reduced to <1 M by ultrafiltration and dilution and the preproinsulin-S-sulfonate is isolated by precipitation at pH 4 and finally dried.

For the formation of the correct disulfide bridges, as are present in natural proinsulin, the preproinsulin-S-sulfonate is dissolved at pH 10.8, in a buffer which contains 20 mM glycine, at a concentration of 0.3 g/l, treated with mercaptoethanol (approximately 25–50 mol/mol of preproinsulin) and stirred overnight at 4° C. The batch is then adjusted to pH 3.5 with phosphoric acid and centrifuged. The preproinsulin contained in the supernatant is adjusted to pH 8.2 for conversion into insulin after addition of tris (25 mM) and treated with trypsin (1.5 mg/g of preproinsulin). The course of the proteolytic cleavage is monitored by means of reversed phase HPLC. After approximately 6 hours, the batch contains a high content of His(B0),des(B30)-insulin. The reaction is ended by acidification to pH 3.5. The insulin analog is purified by ion-exchange chromatography (S-Hyper-D, Sepracor) and reversed phase chromatography (PLRP-S RP300, Polymer Laboratories). The ion-exchange chromatography is carried out in a buffer which contains 30% 2-propanol and 50 mM lactic acid (pH 3.5). The bound insulin is eluted by a linear gradient of 0 to 0.5 M NaCl. The reversed phase chromatography is carried out in 0.1% trifluoroacetic acid, to which increasing amounts of acetonitrile are admixed for elution. The product is isolated by precipitation at pH 5.4 and lyophilized.

EXAMPLE 7

Formulation of Insulin Analogs for Parenteral Administration

The preparations contain, per ml, 40 or 100 IU of insulin (1 IU corresponds to approximately 6.2 nmol), 20 mg of 85% glycerol, 2.7 mg of m-cresol and, if appropriate, $zinc^{++}$ (as zinc chloride) in aqueous, sterile solution at pH 4.

EXAMPLE 8

Profile of Action of His(B0),des(B30)-insulin in the Dog 6 dogs (beagles) in each case received subcutaneous administrations of a preparation containing 40 U/ml (Example 7) and the indicated content of zinc. The dose was 0.3 IU/kg. In the further course of the experiment, the concentration of the blood glucose was measured after the times indicated. The values were standardized percentage-wise on the respective starting value and averaged.

| time (hours) | 0 | 1 | 2 | 3 | 4 | 5 | 6 | 7 | 8 | 9 | 10 | 12 |
|---|---|---|---|---|---|---|---|---|---|---|---|---|
| zinc-free | 100 | 59 | 50 | 61 | 75 | 84 | 89 | 98 | 103 | 97 | 104 | 100 |
| 80 µg $zinc^{++}$/ml | 100 | 97 | 83 | 75 | 65 | 56 | 51 | 58 | 68 | 72 | 78 | 82 |

EXAMPLE 9

Zinc Binding of Insulin Analogs

A preparation of insulin (0.3 mM insulin, 0.13 M NaCl, 0.1% phenol, 100 µg/ml $zinc^{++}$ (as zinc chloride), 25 mM tris/HCl, pH 7.4) was extensively dialyzed against zinc-free neutral buffer (3 h against 0.15 M NaCl, 10 mM tris/HCl pH 7.4 at room temperature, 72 hours against 10 mM tris/HCl pH 7.4 at 15° C. and again 16 h against 10 mM tris/HCl pH 7.4 at 15° C.). The dialyzates were then acidified and analyzed. The concentration of insulin was determined by reversed phase HPLC and that of the zinc by atomic absorption spectroscopy. The zinc values were corrected using the zinc content of a control batch which contained no insulin.

| Insulin | Zinc binding mol of zinc/mol of hexamer |
|---|---|
| human insulin | 2.5 |
| His(B3)-insulin | 6.9 |

| Insulin | Zinc binding mol of zinc/mol of hexamer |
|---|---|
| Asp(B3)-insulin | 4.2 |
| His(B0),des(B30)-insulin | 6.8 |

What is claimed is:

1. An insulin analog or a physiologically tolerable salt thereof of the formula I

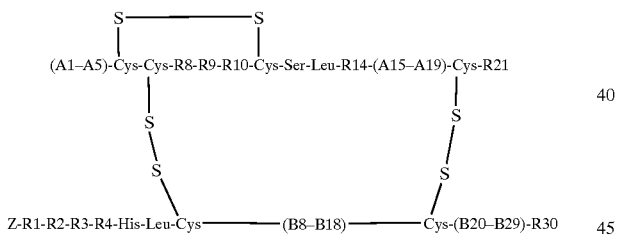

(I)

in which
- (A1–A5) are the amino acids in positions A1 to A5 of the A chain of insulin;
- (A15–A19) are the amino acids in positions A15 to A19 of the A chain of insulin;
- (B8–B18) are the amino acids in positions B8 to B18 of the B chain of insulin;
- (B20–B29) are the amino acids in positions B20 to B29 of the B chain of
- R8 is choosen from Thr and Ala;
- R9 is choosen from Ser and Gly;
- R10 is chosen from Ile and Val;
- R14 is chosen from Tyr, His, Asp, and Glu;
- R21 is chosen from Asn, Asp, Gly, Ser, Thr, Ala, Glu, and Gln;
- R1 is chosen from any genetically encodable amino acid and a hydrogen atom, or is absent;
- R2 is chosen from Val, Ala, and Gly;
- R3 is chosen from Asn, His, Glu, and Asp;
- R4 is chosen from Ala, Ser, Thr, Asn, Asp, Gln, Gly, and Glu;
- R30 is chosen from any genetically encodable amino acid and —OH;
- Z is chosen from a hydrogen atom and a peptide having 1 to 4 genetically encodable amino acids, comprising 1 to 4 histidines (His);
- with the proviso that (1) when Z is a hydrogen atom, R1 or R3 is chosen from His, Glu, and Asp, and when R1 is a neutral or negatively charged amino acid, R3 is His; or (2) when Z is a hydrogen atom, R14 is chosen from His, Asp and Glu; and
- with the further proviso that when in formula I R3, R3 in combination with R21, or R3 in combination with R4, differ from human insulin, the insulin analog or the physiologically tolerable salt thereof of the formula I contains at least one additional variation from human insulin.

2. An insulin analog or a physiologically tolerable salt thereof as claimed in claim 1, wherein R8 is Thr, R9 is Ser, and R10 is Ile.

3. The insulin analog or a physiologically tolerable salt thereof as claimed in claim 1, wherein R1 is chosen from Phe, His, Asn, Asp, and Gly.

4. The insulin analog or a physiologically tolerable salt thereof as claimed in claim 1, wherein R30 is chosen from Thr, Ala, and Ser.

5. The insulin analog or a physiologically tolerable salt thereof as claimed in claim 1, wherein R21 is Asn and R1 is Phe.

6. The insulin analog or a physiologically tolerable salt thereof as claimed in claim 1, wherein R2 is Val, R3 is Asn, and R4 is Gln.

7. The insulin analog or a physiologically tolerable salt thereof as claimed in claim 1, wherein R14 is Tyr.

8. The insulin analog or a physiologically tolerable salt thereof as claimed in claim 1, wherein R30 is Thr.

9. The insulin analog or a physiologically tolerable salt thereof as claimed in claim 1, wherein Z is His.

10. An insulin analog or a physiologically tolerable salt thereof as claimed in claim 9, wherein the B chain has the sequence of SEQ ID NO:4.

11. A process for the preparation of an insulin analog or a physiologically tolerable salt thereof as claimed in claim 1, comprising:

(1) the construction of an expression vector comprising a DNA sequence which encodes a precursor of the insulin analog comprising the amino acid sequence of formula II

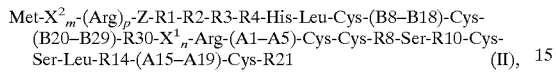

Met-$X^2_m$-(Arg)$_p$-Z-R1-R2-R3-R4-His-Leu-Cys-(B8–B18)-Cys-(B20–B29)-R30-$X^1_n$-Arg-(A1–A5)-Cys-Cys-R8-Ser-R10-Cys-Ser-Leu-R14-(A15–A19)-Cys-R21     (II), in which $X^1_n$ is a peptide chain having n amino acids, where n is an integer from 0 to 34, $X^2_m$ is a peptide chain having m amino acids, wherein m is an integer from 0 to 20, P is 0, 1, or 2, R30 is chosen from any genetically encodable amino acid or is absent, and Z is absent or is a peptide having 1 to 4 genetically encodable amino acids, comprising 1 to 4 histidines (His);

and wherein the other variables are defined in claim 1, and the provisos of claim 1 also apply;

(2) the expression of said expression vector in a host cell; and (3) release of the insulin analog from its precursor using chemical and/or enzymatic methods.

12. A process as claimed in claim 11, wherein the host cell is a bacterium.

13. The process as claimed in claim 12, wherein the bacterium is *E. coli*.

14. The process as claimed in claim 11, wherein the host cell is a yeast.

15. The process as claimed in claim 14, wherein the yeast is *Saccharomyces cerevisiae*.

16. The process as claimed in claim 11 for the preparation of an insulin analog, wherein the precursor has the sequence of SEQ ID NO:7.

17. A precursor of the insulin analog comprising the amino acid sequence of formula II

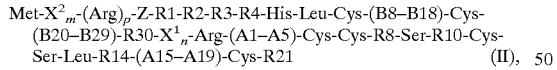

Met-$X^2_m$-(Arg)$_p$-Z-R1-R2-R3-R4-His-Leu-Cys-(B8–B18)-Cys-(B20–B29)-R30-$X^1_n$-Arg-(A1–A5)-Cys-Cys-R8-Ser-R10-Cys-Ser-Leu-R14-(A15–A19)-Cys-R21     (II), in which $X^1_n$ is a peptide chain having n amino acids, where n is an integer from 0 to 34, $X^2_m$ is a peptide chain having m amino acids, wherein m is an integer from 0 to 20, P is 0, 1, or 2, R30 is chosen from any genetically encodable amino acid or is absent, and Z is absent or is a peptide having 1 to 4 genetically encodable amino acids, comprising 1 to 4 histidines (His);

and wherein the other variables are defined in claim 1, and the provisos of claim 1 also apply.

18. A precursor of the insulin analog as set forth in claim 17, wherein the precursor of the insulin analog has the sequence of SEQ ID NO:7.

19. A DNA sequence that encodes the precursor of the insulin analog as claimed in claim 17.

20. A DNA sequence that encodes the precursor of the insulin analog as claimed in claim 18.

21. An expression vector comprising the DNA sequence as claimed in claim 19.

22. A host cell transformed with the expression vector as claimed in claim 21.

23. A pharmaceutical preparation comprising at least one insulin analog or physiologically tolerable salt thereof as claimed in claim 1.

24. The pharmaceutical preparation as claimed in claim 23, wherein the insulin analog and/or the physiologically tolerable salt thereof is in a dissolved, amorphous, and/or crystalline form.

25. The pharmaceutical preparation as claimed in claim 43 or 24, further comprising a depot auxiliary.

26. The pharmaceutical preparation as claimed in claim 25, wherein the depot auxiliary is protamine sulfate and the insulin analog and/or the physiologically tolerable salt thereof is present in a cocrystallizate with the protamine sulfate.

27. The pharmaceutical preparation as claimed in claim 23, further comprising unmodified human insulin.

28. The pharmaceutical preparation as claimed in claim 23, wherein the pharmaceutical preparation comprises more than one insulin analog.

29. The pharmaceutical preparation as claimed in claim 28, wherein at least one insulin analog is Gly(A21)-Arg(B31)-Arg(B32)-human insulin.

30. An injectable solution having insulin activity, comprising the pharmaceutical preparation as claimed in claim 23, in dissolved form.

31. The injectable solution as claimed in claim 30, further comprising 1 µg to 2 mg of zinc per ml.

32. The injectable solution as claimed in claim 31, wherein said zinc is present in a quantity ranging from 5 µg to 200 µg per ml.

33. An insulin-zinc complex comprising an insulin hexamer and 4 to 10 zinc ions per insulin hexamer, wherein the insulin hexamer consists of six molecules of an insulin analog of the formula I

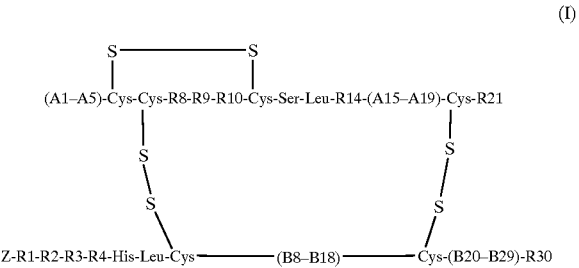

in which (A1–A5) are the amino acids in the positions A1 to A5 of the A chain of insulin;

(A15–A19) are the amino acids in the positions A15 to A19 of the A chain of insulin;

(B8–B18) are the amino acids in the positions B8 to B18 of the B chain of insulin;

(B20–B29) are the amino acids in the positions B20 to B29 of the A chain of insulin;

R8 is chosen from Thr and Ala;

R9 is chosen from Ser and Gly;

R10 is chosen from Ile and Val;

R14 is chosen from Tyr, His, Asp, and Glu;

R21 is chosen from Asn, Asp, Gly, Ser, Thr, Ala, Glu, and Gln;

R1 is chosen from any genetically encodable amino acid and a hydrogen atom, or is absent;

R2 is chosen from Val, Ala, and Gly;

R3 is chosen from Asn, His, Glu, and Asp;

R4 is chosen from Ala, Ser, Thr, Asn, Asp, Gln, Gly, and Glu;

R30 is chosen from any genetically encodable amino acid and OH;

Z is chosen from a hydrogen atom and a peptide having 1 to 4 genetically encodable amino acids, comprising 1 to 4 histidines (His).

34. The insulin-zinc complex as claimed in claim 33, comprising 5 to 8 zinc ions per insulin hexamer.

35. The insulin-zinc complex as claimed in claim 33, wherein the B chain of the insulin analog of the formula I has the sequence of SEQ ID NO:11.

36. A pharmaceutical preparation comprising at least one insulin-zinc complex as claimed in claim 33.

37. A pharmaceutical preparation comprising an acidic solution of at least one insulin analog as claimed in claim 33 and/or a physiologically tolerable salt thereof with the appropriate amount of zinc ions forming the insulin-zinc complex.

38. The pharmaceutical preparation as claimed in claim 37, wherein the B chain of said at least one insulin analog and/or a physiologically tolerable salt thereof is chosen from SEQ ID NO:10 and SEQ ID NO:11.

39. A pharmaceutical preparation comprising the insulin-zinc complex as claimed in claim 36, wherein said preparation is in dissolved, amorphous and/or crystalline form.

40. An injectable solution having insulin activity, comprising the pharmaceutical preparation as claimed in claim 39 in dissolved form.

41. The injectable solution as claimed in claim 40, further comprising from 1 $\mu$g to 2 mg of zinc per ml.

42. The injectable solution as claimed in claim 41, wherein said zinc is present in a quantity ranging from 5 $\mu$g to 200 $\mu$g of zinc per ml.

43. A method for preparing a pharmaceutical preparation comprising adding at least one insulin analog or a physiologically tolerable salt thereof of the formula I as claimed in claim 1 to a pharmaceutically acceptable carrier.

44. A method for preparing a pharmaceutical preparation comprising adding at least one insulin-zinc complex comprising an insulin hexamer and 4 to 10 zinc ions per insulin hexamer as claimed in claim 33 to a pharmaceutically acceptable carrier.

* * * * *

SEQUENCE LISTING

<160> NUMBER OF SEQ ID NOS: 15

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
 1               5                  10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Homo sapiens

<400> SEQUENCE: 3

His Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys
            20                  25                  30

<210> SEQ ID NO 4
<211> LENGTH: 31
<212> TYPE: PRT
<213> ORGANISM: Homo sapiens

<400> SEQUENCE: 4

His Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr
            20                  25                  30

<210> SEQ ID NO 5
<211> LENGTH: 32
<212> TYPE: PRT

-continued

```
<213> ORGANISM: Homo sapiens

<400> SEQUENCE: 5

His Ala Phe Val Asn Gln His Leu Cys Gly Ser His Leu Val Glu Ala
 1               5                  10                  15

Leu Tyr Leu Val Cys Gly Glu Arg Gly Phe Phe Tyr Thr Pro Lys Thr
            20                  25                  30

<210> SEQ ID NO 6
<211> LENGTH: 32
<212> TYPE: PRT
<213> ORGANISM: Homo sapiens

<400> SEQUENCE: 6

His Ala Ala Phe Val Asn Gln His Leu Cys Gly Ser His Leu Val Glu
 1               5                  10                  15

Ala Leu Tyr Leu Val Cys Gly Glu Arg Gly Phe Phe Tyr Thr Pro Lys
            20                  25                  30

<210> SEQ ID NO 7
<211> LENGTH: 98
<212> TYPE: PRT
<213> ORGANISM: Homo sapiens

<400> SEQUENCE: 7

Met Ala Thr Thr Ser Thr Gly Asn Ser Ala Arg His Phe Val Asn Gln
 1               5                  10                  15

His Leu Cys Gly Ser His Leu Val Glu Ala Leu Tyr Leu Val Cys Gly
            20                  25                  30

Glu Arg Gly Phe Phe Tyr Thr Pro Lys Thr Arg Arg Glu Ala Glu Asp
        35                  40                  45

Pro Gln Val Gly Gln Val Glu Leu Gly Gly Pro Gly Ala Gly Ser
    50                  55                  60

Leu Gln Pro Leu Ala Leu Glu Gly Ser Leu Gln Lys Arg Gly Ile Val
 65                  70                  75                  80

Glu Gln Cys Cys Thr Ser Ile Cys Ser Leu Tyr Gln Leu Glu Asn Tyr
                85                  90                  95

Cys Asn

<210> SEQ ID NO 8
<211> LENGTH: 99
<212> TYPE: PRT
<213> ORGANISM: Homo sapiens

<400> SEQUENCE: 8

Met Ala Thr Thr Ser Thr Gly Asn Ser Ala Arg His Ala Phe Val Asn
 1               5                  10                  15

Gln His Leu Cys Gly Ser His Leu Val Glu Ala Leu Tyr Leu Val Cys
            20                  25                  30

Gly Glu Arg Gly Phe Phe Tyr Thr Pro Lys Thr Arg Arg Glu Ala Glu
        35                  40                  45

Asp Pro Gln Val Gly Gln Val Glu Leu Gly Gly Pro Gly Ala Gly
    50                  55                  60

Ser Leu Gln Pro Leu Ala Leu Glu Gly Ser Leu Gln Lys Arg Gly Ile
 65                  70                  75                  80

Val Glu Gln Cys Cys Thr Ser Ile Cys Ser Leu Tyr Gln Leu Glu Asn
                85                  90                  95

Tyr Cys Asn
```

<210> SEQ ID NO 9
<211> LENGTH: 100
<212> TYPE: PRT
<213> ORGANISM: Homo sapiens

<400> SEQUENCE: 9

Met Ala Thr Thr Ser Thr Gly Asn Ser Ala Arg His Ala Ala Phe Val
 1               5                  10                  15

Asn Gln His Leu Cys Gly Ser His Leu Val Glu Ala Leu Tyr Leu Val
             20                  25                  30

Cys Gly Glu Arg Gly Phe Phe Tyr Thr Pro Lys Thr Arg Arg Glu Ala
         35                  40                  45

Glu Asp Pro Gln Val Gly Gln Val Glu Leu Gly Gly Pro Gly Ala
     50                  55                  60

Gly Ser Leu Gln Pro Leu Ala Leu Glu Gly Ser Leu Gln Lys Arg Gly
 65                  70                  75                  80

Ile Val Glu Gln Cys Cys Thr Ser Ile Cys Ser Leu Tyr Gln Leu Glu
                 85                  90                  95

Asn Tyr Cys Asn
            100

<210> SEQ ID NO 10
<211> LENGTH: 30
<212> TYPE: PRT
<213> ORGANISM: Homo sapiens

<400> SEQUENCE: 10

Phe Val His Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
             20                  25                  30

<210> SEQ ID NO 11
<211> LENGTH: 30
<212> TYPE: PRT
<213> ORGANISM: Homo sapiens

<400> SEQUENCE: 11

Phe Val Asp Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
             20                  25                  30

<210> SEQ ID NO 12
<211> LENGTH: 67
<212> TYPE: DNA
<213> ORGANISM: Artificial Sequence
<220> FEATURE:
<223> OTHER INFORMATION: Description of Artificial Sequence: Synthetic
      DNA fragment

<400> SEQUENCE: 12
catggcaaca acatcaacag gaaattcggc gcgctttgtg caccagcacc tgtgcggctc     60
ccaccta                                                              67

<210> SEQ ID NO 13
<211> LENGTH: 41
<212> TYPE: DNA
<213> ORGANISM: Artificial Sequence
<220> FEATURE:

```
<223> OTHER INFORMATION: Description of Artificial Sequence: Synthetic
      DNA fragment

<400> SEQUENCE: 13
cgcgccactt tgttaaccag cacctgtgcg gctcccacct a                           41

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      DNA fragment

<400> SEQUENCE: 14
cgcgccacgc ttttgttaac cagcacctgt gcggctccca ccta                       44

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA fragment

<400> SEQUENCE: 15
cgcgccacgc tgcttttgtt aaccagcacc tgtgcggctc ccaccta                    47
```